United States Patent
Xiaodong et al.

(10) Patent No.: US 7,147,370 B2
(45) Date of Patent: Dec. 12, 2006

(54) LIGHT IRRADIATOR, LAMP ASSEMBLY, AND X-RAY APPARATUS

(75) Inventors: Xu Xiaodong, Beijing (CN); Tan Yongtao, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/946,763

(22) Filed: Sep. 22, 2004

(65) Prior Publication Data

US 2005/0069092 A1    Mar. 31, 2005

(30) Foreign Application Priority Data

Sep. 29, 2003    (CN) ................. 03 1 64889

(51) Int. Cl.
*A61B 6/08*    (2006.01)
(52) U.S. Cl. ........................ 378/206; 378/205
(58) Field of Classification Search ........ 378/205–206, 378/196–197, 193; 362/529, 528, 525, 523
See application file for complete search history.

(56) References Cited

U.S. PATENT DOCUMENTS

| 4,135,785 A | 1/1979 | Bernolak et al. |
| 4,167,675 A | 9/1979 | Stodberg et al. |
| 4,426,726 A | 1/1984 | Cheetham |
| 4,472,826 A | 9/1984 | van de Ven |
| 4,502,147 A | 2/1985 | Michaels |
| 5,212,720 A * | 5/1993 | Landi et al. ................. 378/206 |
| 5,870,450 A * | 2/1999 | Khutoryansky et al. .... 378/197 |
| 6,104,778 A | 8/2000 | Murad |

FOREIGN PATENT DOCUMENTS

JP        55-115001        9/1980

* cited by examiner

Primary Examiner—Edward J. Glick
Assistant Examiner—Hoon Song
(74) Attorney, Agent, or Firm—Carl B. Horton, Esq.; Armstrong Teasdale LLP

(57) ABSTRACT

A light irradiator that includes a light source, a light source supporting device which supports the light source replaceably, a first support device which supports the light source supporting device in such a manner that the position of the light source supporting device can be adjusted in a first direction out of three directions perpendicular to one another, a second support device which supports the first support device in such a manner that the position of the first support device can be adjusted in a second direction out of the three directions, and a third support device which can be mounted removably in a predetermined positional relation to a member to which it is to be mounted, the third support device supporting the second support device in such a manner that the position of the second support device can be adjusted in a third direction out of the three directions.

6 Claims, 3 Drawing Sheets

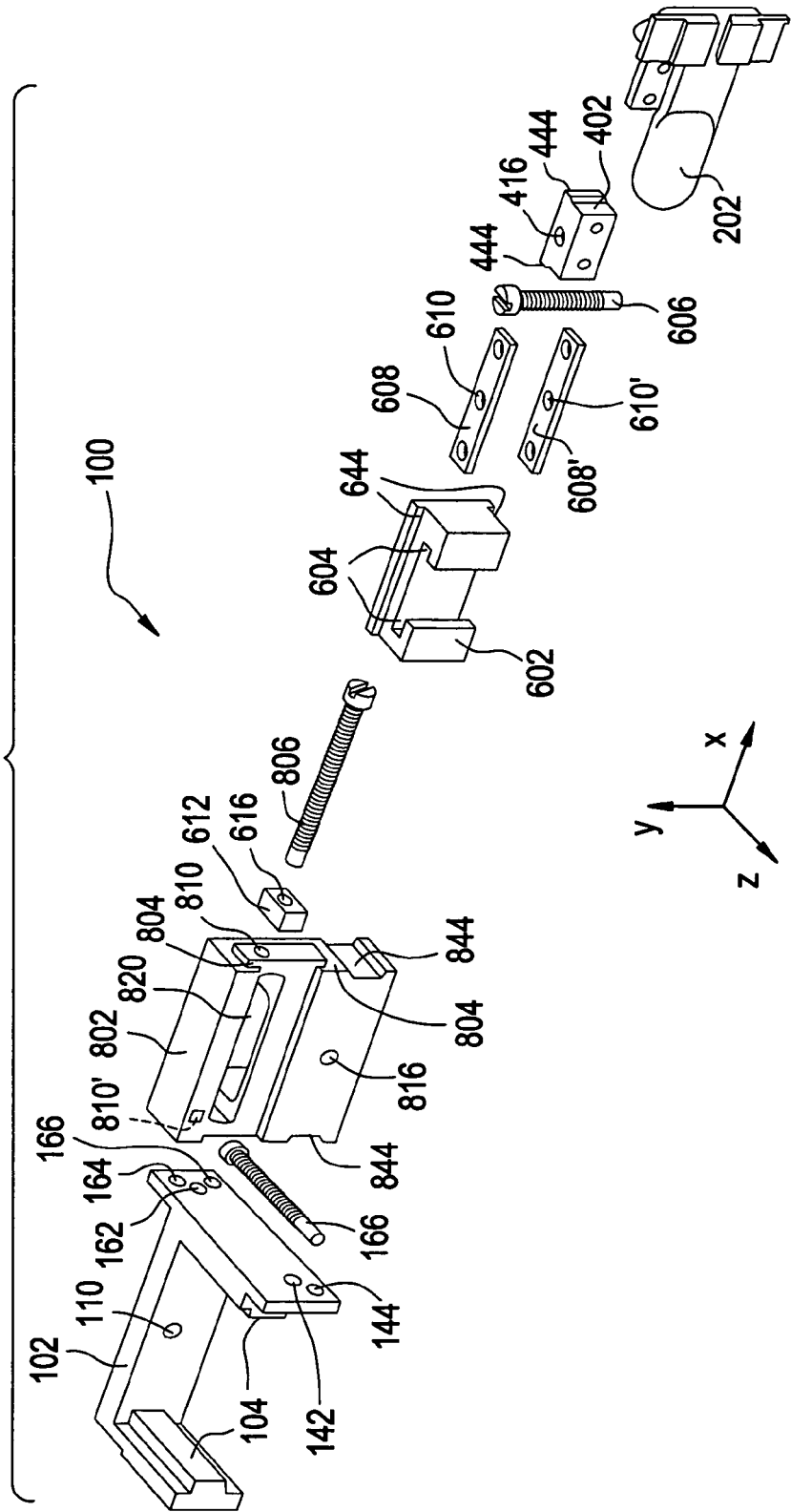

LIGHT IRRADIATOR, LAMP ASSEMBLY, AND X-RAY APPARATUS

CROSS REFERENCE TO RELATED APPLICATIONS

This application claims the benefit of Japanese Application No. 03164889.4 filed Sep. 29, 2003.

BACKGROUND OF THE INVENTION

The present invention relates to a light irradiator, a lamp assembly, and an X-ray apparatus. Particularly, the invention is concerned with a light irradiator which makes aiming with use of light prior to irradiation of X-ray, as well as a lamp assembly for the light irradiator and an X-ray apparatus provided with the light irradiator.

In an X-ray apparatus, aiming is made using light prior to the irradiation of X-ray, and X-ray is radiated after completion of the aiming (see, for example, patent literature 1).

[Patent Literature] Japanese Published Unexamined Patent Application No. Sho 55-115001 (page 1, FIG. 1).

Since a light source has a service life, it is replaced in an appropriate period. With replacement of the light source, the optical system concerned undergoes a change of alignment, so re-adjustment is absolutely necessary. A fairly high-level of skill is required for the re-adjustment and it is difficult for a user to make re-adjustment. It is necessary to have a special trader come to an operation side of the X-ray apparatus concerned and make re-adjustment.

SUMMARY OF THE INVENTION

Therefore, it is an object of the present invention to provide a light irradiator which permits a user to replace a light source, a lamp assembly for the light irradiator, and an X-ray apparatus provided with the light irradiator.

(1) In one aspect of the present invention for solving the above-mentioned problem the invention resides in a light irradiator comprising a light source, a light source supporting means which supports the light source replaceably, a first support means which supports the light source supporting means in such a manner that the position of the light source supporting means can be adjusted in a first direction out of three directions perpendicular to one another, a second support means which supports the first support means in such a manner that the position of the first support means can be adjusted in a second direction out of the three directions, a third support means which supports the second support means in such a manner that the position of the second support means can be adjusted in a third direction out of the three directions, a base to which the third support means is mounted removably in a predetermined positional relation, and a reflecting mirror provided on the base so as to deflect the direction of light emitted from the light source.

(2) In another aspect of the present invention for solving the above-mentioned problem the invention resides in a lamp assembly comprising a light source, a light source supporting means which supports the light source replaceably, a first support means which supports the light source supporting means in such a manner that the position of the light source supporting means can be adjusted in a first direction out of three directions perpendicular to one another, a second support means which supports the first support means in such a manner that the position of the first support means can be adjusted in a second direction out of the three directions, a third support means which can be mounted removably in a predetermined positional relation to a member to which it is to be mounted, the third support means supporting the second support means in such a manner that the position of the second support means can be adjusted in a third direction out of the three directions.

(3) In a further aspect of the present invention for solving the above-mentioned problem the invention resides in an X-ray apparatus comprising an X-ray tube, a collimator for collimating X-ray which is radiated from the X-ray tube to an object to be radiographed, and a light irradiator which radiates light for aiming to the object to be radiographed, wherein as the light irradiator there is used the light irradiator described in (1).

According to the present invention in each of the above aspects, the light source is supported replaceably by the light source supporting means, the light source supporting means is supported by the first support means so that the position thereof can be adjusted in a first direction out of three mutually perpendicular directions, the first support means is supported by the second support means so that the position thereof can be adjusted in a second direction out of the three directions, and the second support means is supported by the third support means so that the position thereof can be adjusted in a third direction out of the three directions. Therefore, a three-dimensional position of a focus of the light source in such a structure can be adjusted beforehand on the manufacturer side. Accordingly, all that is required for a user is only mounting such a structure to the base to which a positional relation is determined in advance.

For facilitating the adjustment of the three-dimensional position it is preferable that the first support means, the second support means, and the third support means be each provided with a feed screw for position adjustment.

For facilitating the adjustment of the three-dimensional position it is preferable that the first support means, the second support means, and the third support means be each provided with a guide rail for position adjustment.

For radiating light in a base transmitting direction it is preferable for the base to have an irradiation port for the light reflected by the reflecting mirror. For disposing the light source just sideways with respect to the direction of light irradiation it is preferable that the reflecting mirror deflect the light from the light source at right angles.

According to the present invention, there can be provided a light irradiator which permits the user to replace the light source, a lamp assembly for the light irradiator, and an X-ray apparatus provided with the light irradiator.

Further objects and advantages of the present invention will be apparent from the following description of the preferred embodiments of the invention as illustrated in the accompanying drawings.

BRIEF DESCRIPTION OF THE DRAWINGS

FIG. 4 is an exploded view of the light assembly.

DETAILED DESCRIPTION OF THE INVENTION

Figure 1:
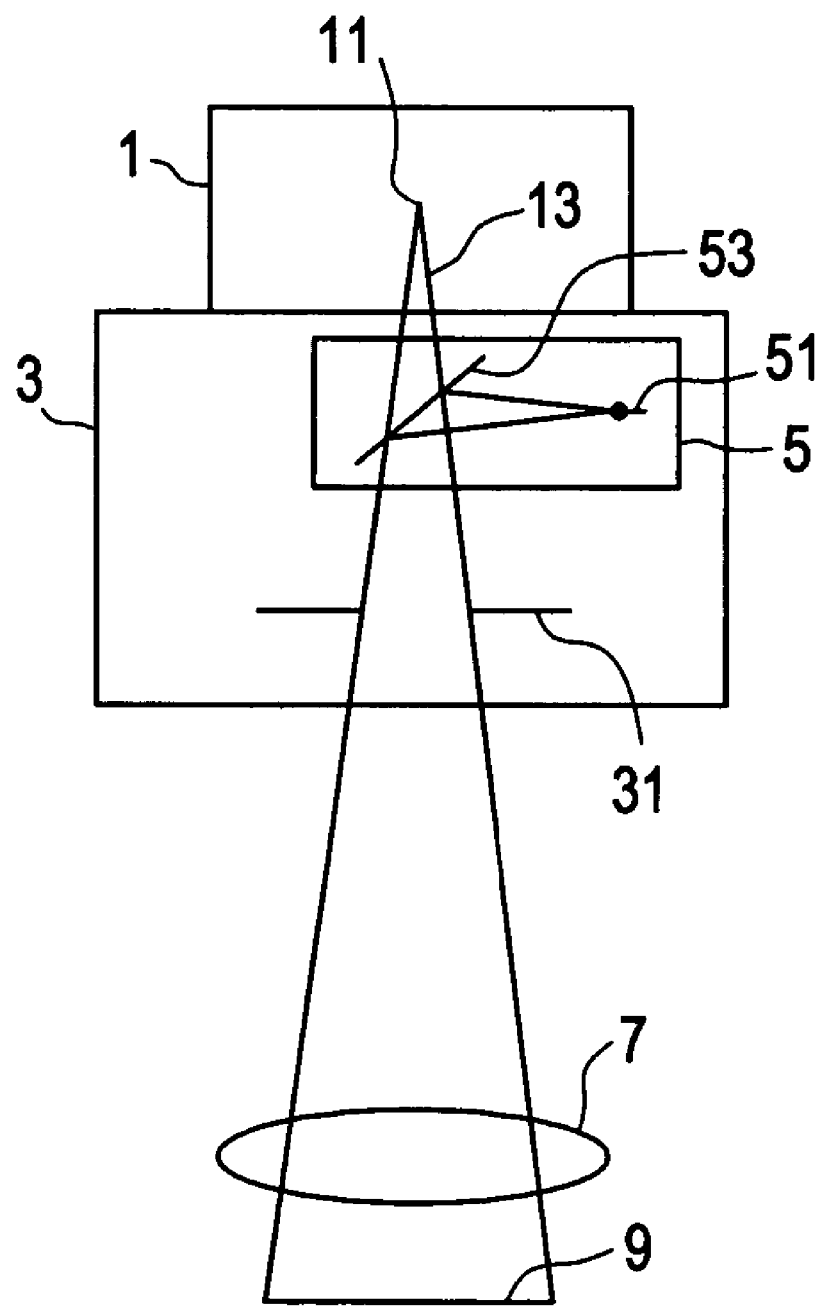
FIG. 1 illustrates a schematic construction according to an embodiment of the present invention.

An embodiment of the present invention will be described in detail hereinunder with reference to the accompanying drawings. FIG. 1 illustrates a schematic construction of an X-ray apparatus embodying the present invention. The illustrated construction of the X-ray apparatus is an example of the apparatus defined in the present invention.

In this X-ray apparatus, as shown in the same figure, X-ray 13 emitted from an X-ray focus 11 of an X-ray tube 1 is collimated by a blade 31 disposed within a collimator box 3, then is applied to an object 7 to be radiographed and is detected by a detector 9.

The collimator box 3 is internally provided with a light irradiator 5. The light irradiator 5, which is positioned between the X-ray focus 11 and the blade 31, has a light source 51 and a reflecting mirror 53. The reflecting mirror 53, which is inserted into a traveling route of the X-ray 13, deflects the direction of visible light emitted from the light source 51 and directs the visible light in the same direction as the irradiation direction of the X-ray 13. According to this construction it is possible to effect aiming with visible light prior to X-ray irradiation.

Figure 2:
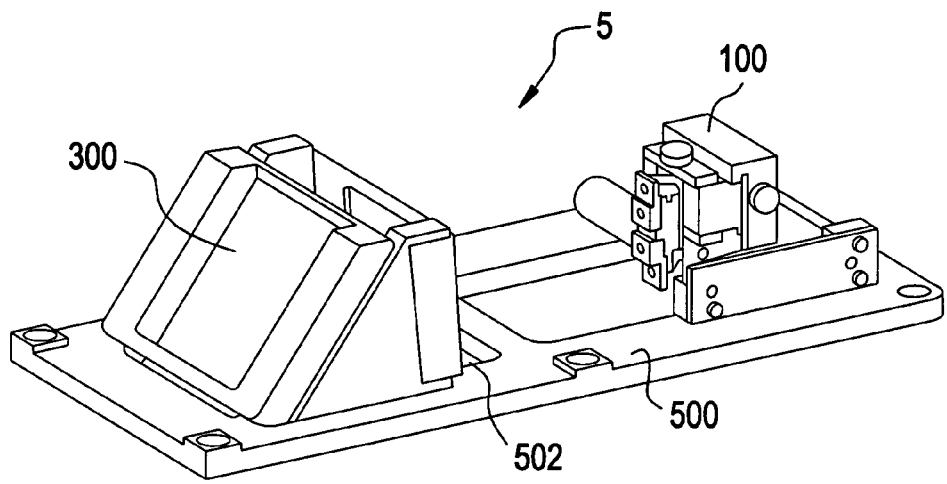
FIG. 2 illustrates an appearance of a light irradiator.

FIG. 2 shows an appearance of the light irradiator 5, whose construction is an example of the light irradiator defined in the present invention.

In the light irradiator 5, as shown in the same figure, a lamp assembly 100 and a mirror 300 are mounted on a base 500. The lamp assembly 100 and the mirror 300 are opposed to each other in the horizontal direction. The mirror 300 is an example of the reflecting mirror defined in the present invention and the base 500 is an example of the base defined in the present invention.

The base 500 has a light irradiation port 502 for downward radiation of light emitted from the lamp assembly 100 and reflected by the mirror 300. With light irradiation port 502, light can be directed in a direction to pass through the base 500. The light irradiation port 502 is an example of the irradiation port defined in the present invention.

The mirror 300 is positioned at an angle of 45° relative to a horizontal plane to deflect the direction of light from the lamp assembly 100 at right angles. Consequently, the lamp assembly 100 can be disposed just sideways with respect to the final light irradiation direction (vertically downward). When the light irradiator 5 is disposed within the collimator box in the X-ray irradiator, the lamp assembly 100 is not an obstacle to X-ray irradiation.

Figure 3:
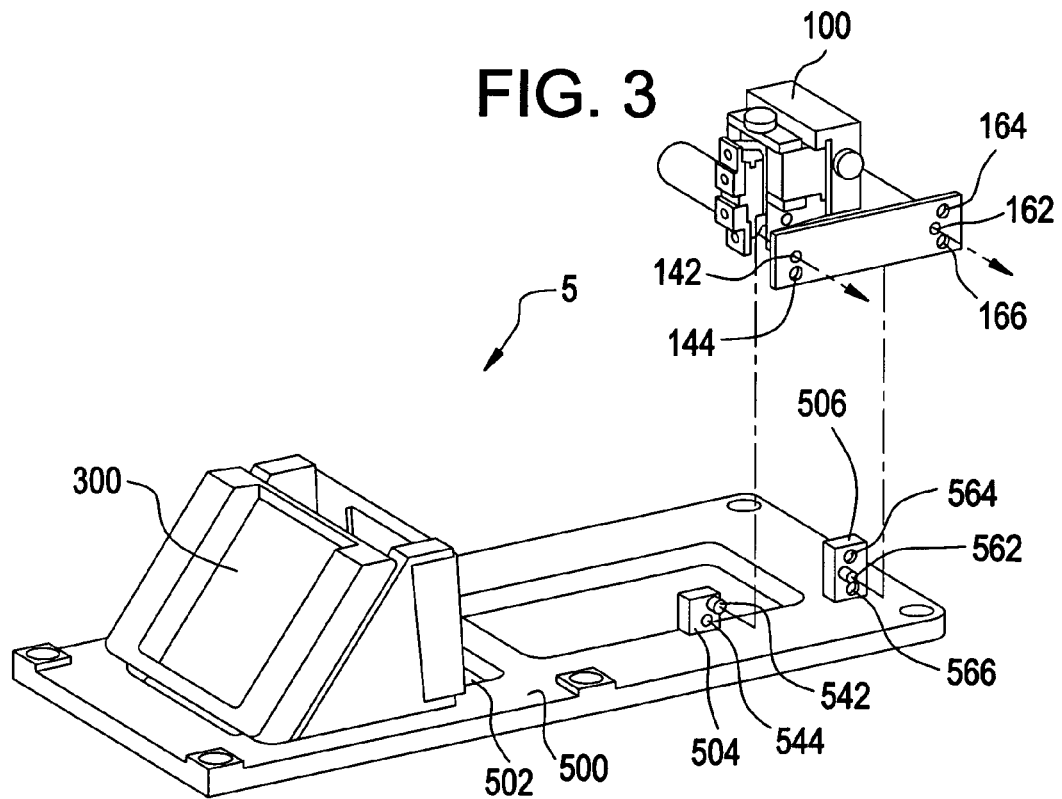
FIG. 3 illustrates the light irradiator with a lamp assembly separated therefrom.

The lamp assembly 100 can be mounted to the base 500 removably. FIG. 3 shows a separated state of the lamp assembly 100 and the base 500 from each other. As shown in the same figure, the base 500 has two pillars 504 and 506 for mounting the lamp assembly 100, and a base portion of the lamp assembly 100 is screwed to outer side faces of those pillars.

At this time, pins 542 and 562 provided perpendicularly on the outer side faces of the pillars 504 and 506 and holes 142 and 162 formed in the base portion of the lamp assembly 100 are fitted together, whereby there is made positioning of the lamp assembly 100 with respect to the base 500. In this state, screwing is made through tapped holes 544, 564 and 566 respectively formed in outer side faces of the pillars 504 and 506 and holes 144, 164, and 166 formed in the base portion of the lamp assembly 100. A positional relation of the lamp assembly 100 to the base 500 is determined unambiguously by the positioning which utilizes the fitting between the pins 542, 562 and the holes 142, 162.

FIG. 4 is an exploded view of the lamp assembly 100 embodying the present invention. The illustrated construction of the lamp assembly 100 is an example of the lamp assembly defined in the present invention.

In the same figure, three directions perpendicular to one another are assumed to be x, y, and z, respectively. In the lamp assembly 100, a lamp 202 is attached to a mounting block 402. The mounting is performed using screws or the like so that the lamp 202 can be replaced as necessary. The lamp 202 is an example of the light source defined in the present invention. The mounting block 402 is an example of the light source supporting means defined in the present invention.

The mounting block 402 has a tapped hole 416 which is a through hole extending in the y direction through the mounting block 402. An adjusting screw 606 comes into threaded engagement with the tapped hole 416. The adjusting screw 606 is attached to the y-direction rail block 602 through a pair of mounting plates 608 and 608'. The adjusting screw 606 is loosely fitted in holes 610 and 610' formed in the mounting plates 608 and 608' and does not move in the y direction. Consequently, the mounting block 402 can be moved in the y direction by turning the adjusting screw 606.

The portion consisting of the y-direction rail block 602, the adjusting screw 606 and the mounting plates 608, 608' is an example of the first support means defined in the present invention. The rail portions 604 are an example of the guide rail defined in the present invention. The adjusting screw 606 is an example of the feed screw defined in the present invention.

The y-direction rail block 602 is combined with an x-direction rail block 802. The x-direction rail block 802 has rail portions 804 extending in the x direction, with which are engaged slide portions 644 of the y-direction rail block 602.

In this engaged state, a tapped hole pillar 612 is provided perpendicularly to a back side of the y-direction rail block 602 through a slit 820. A tapped hole 616 is formed in the x direction through the tapped hole pillar 612.

An adjusting screw 806 comes into threaded engagement with the tapped hole 616. The adjusting screw 806 is loosely fitted in holes 810 and 810' formed in the x-direction rail block 802 and does not move in the x direction. Consequently, the y-direction rail block 602 can be moved in the x direction by turning the adjusting screw 806.

The portion consisting of the x-direction rail block 802 and the adjusting screw 806 is an example of the second support means defined in the present invention. The rail portions 804 are an example of the guide rail defined in the present invention. The adjusting screw 806 is an example of the feed screw defined in the present invention.

The x-direction rail block 802 is combined with a z-direction rail block 102. The z-direction rail block 102 has rail portions 104 extending in the z direction, with which are engaged slide portions 844 of the x-direction rail block 802. The x-direction rail block 802 has a tapped hole 816 as a through hole extending in the z direction.

In a combined state of the z-direction rail block 102 with the x-direction rail block 802, an adjusting screw 106 is threadedly engaged with the tapped hole 816 through a hole 110. The adjusting screw 106 is loosely fitted in the hole 110 and does not move in the z direction. Consequently, the x-direction rail block 802 can be moved in the z direction by turning the adjusting screw 106.

The portion consisting of the z-direction rail block 102 and the adjusting screw 106 is an example of the third support means defined in the present invention. The rail portions 104 are an example of the guide rail defined in the present invention. The adjusting screw 106 is an example of the feed screw defined in the present invention.

The z-direction rail block 102 has holes 142, 144, 162, 164, and 166 for mounting thereof to the base 500 of the light irradiator 5. The z-direction lamp assembly 102 corresponds to the base portion of the lamp assembly 100.

In the lamp assembly constructed as above, the position in the y direction of the lamp 202 can be adjusted by turning the adjusting screw 606, the position in the x direction of the lamp 202 can be adjusted by turning the adjusting screw 806, and the position in the z direction of the lamp 202 can be adjusted by turning the adjusting screw 106. That is, it is possible to adjust a three-dimensional position of the lamp 202 in the lamp assembly 100.

The positional adjustment for the lamp 202 is conducted in such a manner that the focus of light assumes a predetermined three-dimensional position. Such an adjustment is made on a manufacturer side of the lamp assembly 100 using a suitable adjusting device when the lamp 202 is mounted to the mounting block 402. The positional adjustment for the lamp 202 is conducted also upon replacement of the lamp 202 with a new one with respect to the lamp assembly 100 which has been recovered by manufacturer, for example, due to failure of the lamp 202.

The lamp assembly 100 after the positional adjustment is mounted to the base 500 of the light irradiator 5 and is used. As shown in FIG. 3, a positional relation of the lamp assembly 100 to the base 500 is determined unambiguously by fitting of the pins 542 and 562 of the pillars 504 and 506 with the holes 142 and 162 formed in the base portion of the lamp assembly 100, so that alignment of the optical system is accomplished merely by mounting the lamp assembly 100 to the base. Therefore, as to the replacement of the lamp assembly 100 in the event of failure of the lamp, the user can do it without asking the trader for the replacement.

Many widely different embodiments of the invention may be configured without departing from the spirit and the scope of the present invention. It should be understood that the present invention is not limited to the specific embodiments described in the specification, except as defined in the appended claims.

The invention claimed is:

1. A light irradiator comprising:
   a light source;
   a light source supporting device which supports the light source replaceably;
   a first support device which supports the light source supporting device, wherein the first support device configured to adjust, in a first direction out of three directions perpendicular to one another, a position of the light source supporting device;
   a second support device which supports the first support device, wherein second support device configured to adjust, in a second direction out of the three directions, a position of the first support device, wherein the second direction is perpendicular to the first direction;
   a third support device which supports the second support device, wherein the third support device configured to adjust, in a third direction out of the three directions, a position of the second support device, wherein the third direction is perpendicular to the first direction and perpendicular to the second direction;
   a base to which the third support device is mounted removably in a predetermined positional relation; and
   a reflecting mirror provided on the base so as to deflect the direction of light emitted from the light source.

2. A light irradiator according to claim 1, wherein the first support device, the second support device, and the third support device are each provided with a feed screw for position adjustment.

3. A light irradiator according to claim 2, wherein the first support device, the second support device, and the third support device are each provided with a guide rail for position adjustment.

4. A light irradiator according to claim 1, wherein the base has an irradiation port for the light reflected by the reflecting mirror.

5. A light irradiator according to claim 1, wherein the reflecting mirror deflects the direction of the light from the light source at right angles.

6. An X-ray apparatus comprising:
   an X-ray tube;
   a collimator for collimating X-ray which is radiated from the X-ray tube to an object to be radiographed; and
   a light irradiator which radiates light for aiming to the object to be radiographed, wherein said light irradiator comprises:
   a light source;
   a light source supporting device which supports the light source replaceably;
   a first support device which supports the light source supporting device, wherein the first support device configured to adjust, in a first direction out of three directions perpendicular to one another, a position of the light source supporting device;
   a second support device which supports the first support device, wherein the second support device configured to adjust, in a second direction out of the three directions, a position of the first support device, wherein the second direction is perpendicular to the first direction;
   a third support device which supports the second support device, wherein the third support device configured to adjust, in a third direction out of the three directions, a position of the second support device, wherein the third direction is perpendicular to the first direction and perpendicular to the second direction;
   a base to which the third support device is mounted removably in a predetermined positional relation; and
   a reflecting mirror provided on the base so as to deflect the direction of light emitted from the light source.

* * * * *

UNITED STATES PATENT AND TRADEMARK OFFICE
CERTIFICATE OF CORRECTION

PATENT NO. : 7,147,370 B2  Page 1 of 1
APPLICATION NO. : 10/946763
DATED : December 12, 2006
INVENTOR(S) : Xiaodong et al.

It is certified that error appears in the above-identified patent and that said Letters Patent is hereby corrected as shown below:

In Claim 1, column 5, line 54, between "wherein" and "second", insert --the--.

Signed and Sealed this

Tenth Day of June, 2008

JON W. DUDAS
*Director of the United States Patent and Trademark Office*